(12) United States Patent
Yamaya

(10) Patent No.: US 10,004,390 B2
(45) Date of Patent: Jun. 26, 2018

(54) WASHING TOOL FOR INSERTION DEVICE

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/457,093

(22) Filed: Mar. 13, 2017

(65) Prior Publication Data

US 2017/0181612 A1    Jun. 29, 2017

Related U.S. Application Data

(63) Continuation of application No. PCT/JP2015/075911, filed on Sep. 11, 2015.

(30) Foreign Application Priority Data

Oct. 15, 2014    (JP) ................................ 2014-210880

(51) Int. Cl.
  *A61B 1/06*    (2006.01)
  *A61B 1/12*    (2006.01)
  *A61B 1/00*    (2006.01)
  *B08B 9/032*    (2006.01)

(52) U.S. Cl.
  CPC .......... *A61B 1/123* (2013.01); *A61B 1/00009* (2013.01); *A61B 1/06* (2013.01); *B08B 9/0321* (2013.01)

(58) Field of Classification Search
  CPC .................................................. A61B 1/123
  See application file for complete search history.

(56) References Cited

FOREIGN PATENT DOCUMENTS

| JP | H03-280925 A | 12/1991 |
|---|---|---|
| JP | H04-314418 A | 11/1992 |
| JP | H08-196505 A | 8/1996 |
| JP | H11-009541 A | 1/1999 |
| JP | 2012-045327 A | 3/2012 |
| WO | 2015/107801 A1 | 7/2015 |

OTHER PUBLICATIONS

International Search Report issued in PCT/JP2015/075911 dated Dec. 15, 2015.
English translation of International Preliminary Report on Patentability dated Apr. 27, 2017 together with the Written Opinion received in related International Application No. PCT/JP2015/075911.

*Primary Examiner* — Jason Ko
(74) *Attorney, Agent, or Firm* — Scully, Scott, Murphy & Presser, P.C.

(57) ABSTRACT

A washing instrument comprises a washing instrument body to which a distal configuration portion of an insertion device is attached, a three-way cock which communicates with both a first washing opening and a second washing opening that spout out a washing liquid at different positions inside a receiving chamber of the distal configuration portion and thus switches communication directions and which adjusts a liquid supply volume, a liquid supply function comprising a syringe coupling portion having a syringe to supply the washing liquid and a check valve, and a movement regulating portion which positions the distal configuration portion at a position where the washing liquid is directly spouted out from the first washing opening and the second washing opening to a swing base that is provided in the receiving chamber and that swings the movement direction of the extension of a treatment instrument.

10 Claims, 8 Drawing Sheets

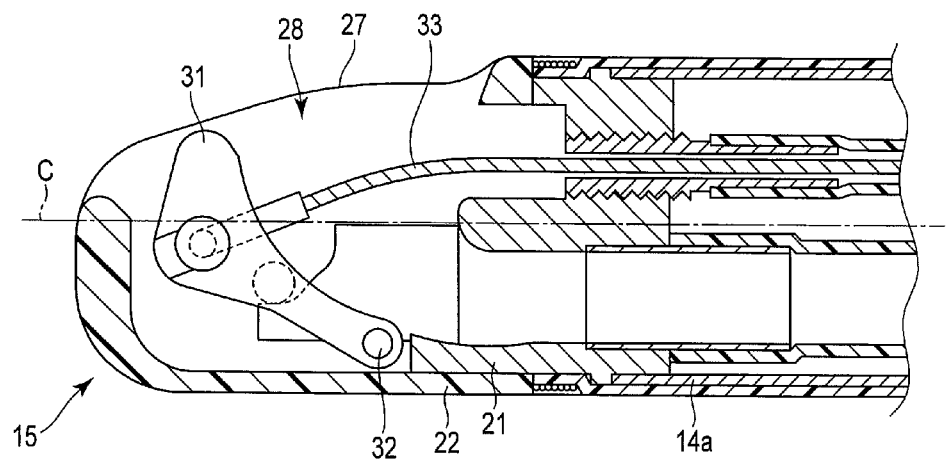
F I G. 3
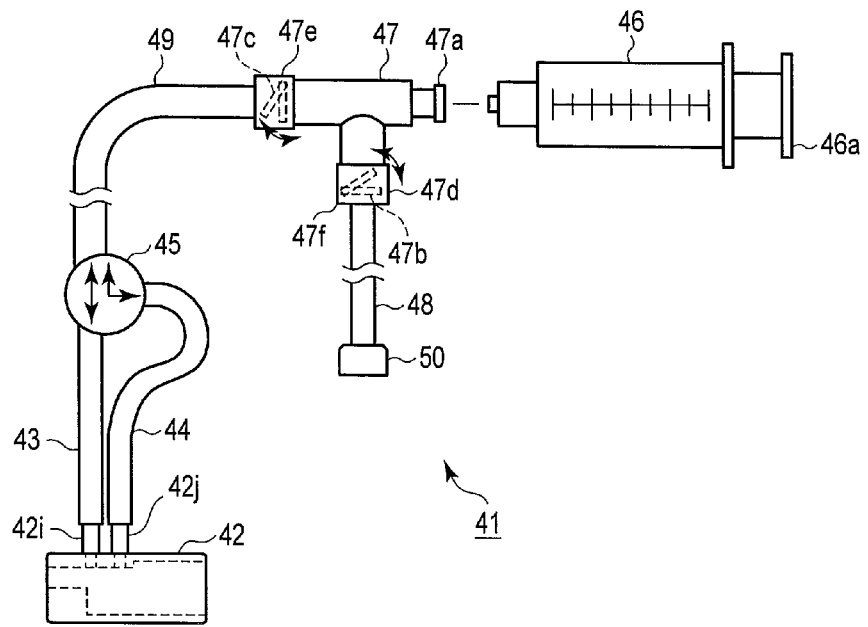
F I G. 4

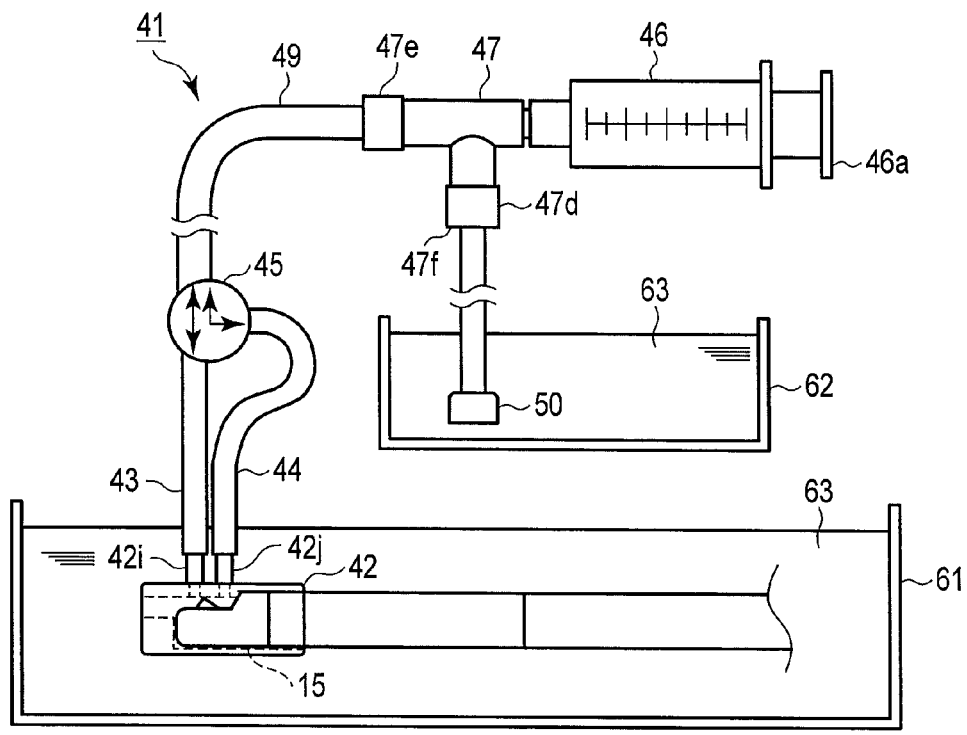
F I G. 5
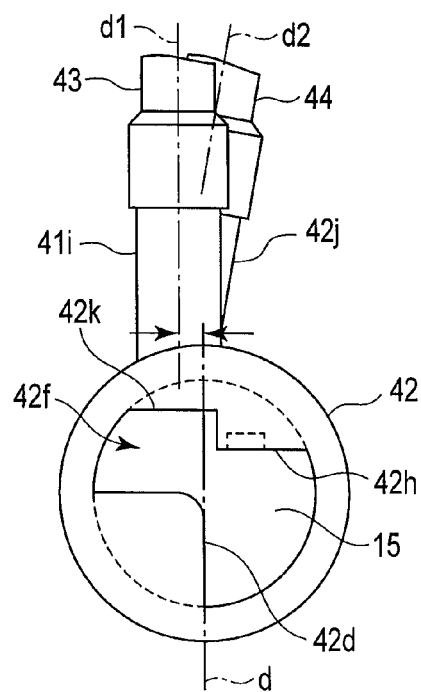
F I G. 6

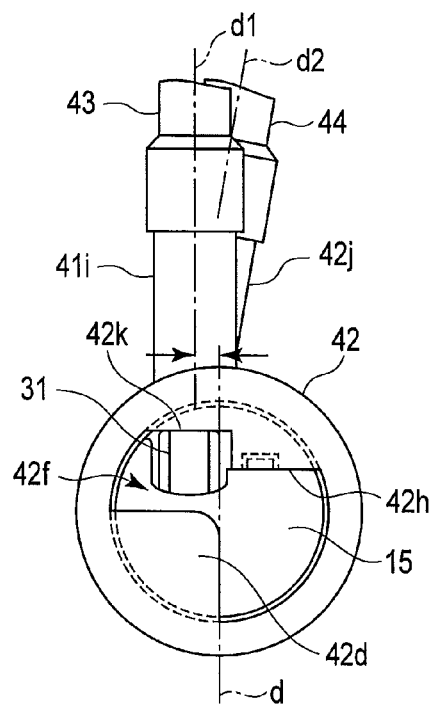
F I G. 7A
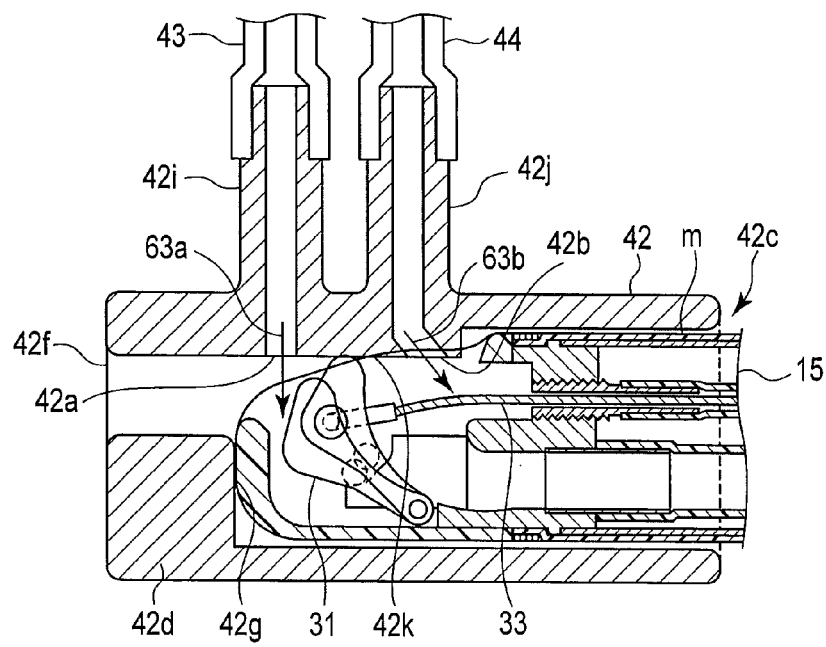
F I G. 7B

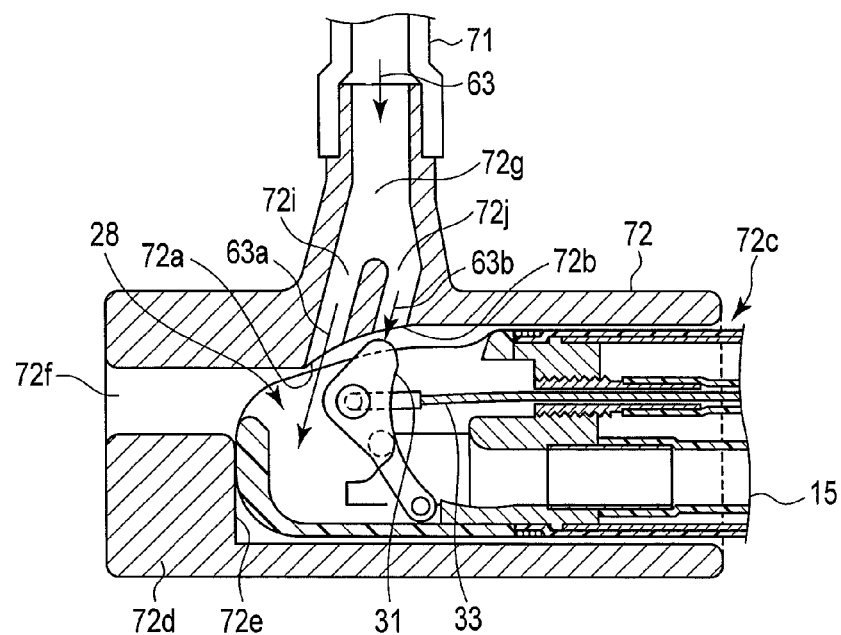
F I G. 10A
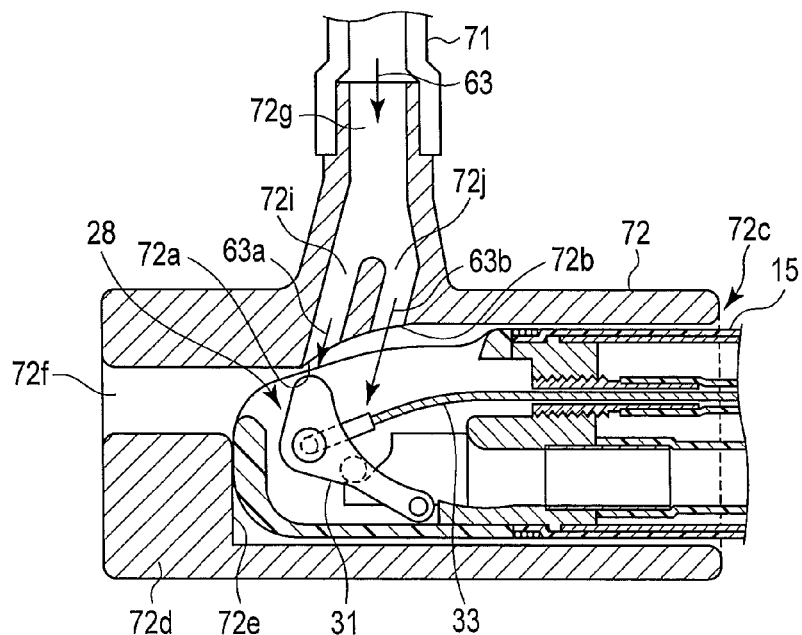
F I G. 10B

WASHING TOOL FOR INSERTION DEVICE

CROSS-REFERENCE TO RELATED APPLICATIONS

This is a Continuation Application of PCT Application No. PCT/JP2015/075911, filed Sep. 11, 2015, which was published under PCT Article 21(2) in Japanese. This application is based upon and claims the benefit of priority from prior the Japanese Patent Application No. 2014-210880 filed Oct. 15, 2014 the entire contents of which are incorporated herein by references.

BACKGROUND OF THE INVENTION

1. Field of the Invention

The present invention relates to a washing instrument for an insertion device provided with a treatment instrument swing base on the distal side thereof.

2. Description of the Related Art

In general, a treatment instrument having various functions, such as a forceps, extends from an aperture section which is made on the distal side from an endoscope body through a channel of an insertion portion. An aperture section is also provided in a part of the circumferential surface side of the distal end of the insertion portion, and there is known a swing mechanism which bends, in a desired direction, the movement direction of the treatment, instrument extending from this aperture section. A swing base for the treatment instrument (or a treatment instrument swing base) is known as a typical swing mechanism. This swing base can rise by the operation of an operation lever provided on an operation portion side, to change the movement direction of a treatment instrument such as a forceps in a desired direction.

If the insertion portion is inserted into a body cavity, bodily fluids and resected living tissues, for example, enter from the aperture section portion in which the swing base is disposed, and adhere to a swing base body and its peripheral part. After the end of a treatment, washing and sterilization of an endoscope are indispensable to prevent infectious diseases. Because of the complicated structure, washing work to completely remove unnecessary objects is troublesome, which is addressed by washing that uses a washing instrument.

For example, a technique regarding the washing of the inside of the distal end of an insertion portion of an endoscope is suggested in Patent Literature 1: Jpn. Pat. Appln. KOKAI Publication No. 08-196505. A hole which communicates with a receiving chamber and which is an attachment opening to attach a washing instrument, to is formed in the front surface of the distal end of the insertion portion of the endoscope. A connection portion of the washing instrument which is attached to this hole has a flow path to supply and suck a washing liquid, and the washing liquid is supplied to and sucked from the inside of the receiving chamber through this flow path to decontaminate the inside of the receiving chamber.

In Jpn. Pat. Appln. KOKAI Publication No. 08-196505, a cover member which covers the entire distal end to make it difficult for the connection portion to come off is suggested as another example. In this cover member, the connection portion which is plugged into the hole that is the attachment opening is formed to protrude in the inner bottom surface of the cover member. That is, if the entire distal end is covered with the cover member, the connection portion having the flow path is attached in a state where the connection portion is in the hole, and the washing liquid is supplied and sucked. In this cover member, a drain opening is also formed at a position corresponding to the aperture section of the receiving chamber.

BRIEF SUMMARY OF THE INVENTION

According to an embodiment of the present invention, there is provided a washing instrument for an insertion device comprising: a housing portion including a cylindrical receiving chamber in which the distal end portion of the insertion device provided with an aperture section in a distal-side circumferential surface thereof fitted; a liquid supply path which allows a fluid for washing to be passed to the housing portion from the outside; a first washing opening which spouts out the fluid from the liquid supply path to the receiving chamber in a first direction that intersects with the longitudinal direction of the housing portion; a second washing opening which spouts out the fluid from the liquid supply path to the receiving chamber in a second direction that intersects with the longitudinal direction of the housing portion; and a movement regulating portion which positions the distal end portion of the insertion device at a position where the fluid spouted out from the first washing opening and the fluid spouted out from the second washing opening directly collide with the distal end portion of the insertion device fitted in the housing portion at different positions inside the aperture section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3 is a diagram showing the configuration of the cross section of a swing base in a falling state in the distal configuration port on shown in FIG. 2A;

FIG. 4 is a diagram showing the external configuration of a washing instrument according to the present embodiment;

FIG. 5 is a diagram showing a state where an insertion device is attached to the washing instrument and thus washed;

FIG. 6 is a diagram in which the washing instrument without the insertion device attached thereto is seen from the front surface side;

FIG. 7A is a diagram in which the washing instrument with the insertion device attached thereto is seen from the front side;

FIG. 7B is a diagram showing the cross section of the washing instrument with the insertion device attached thereto;

FIG. 10A is a diagram showing the cross section of the washing instrument when the insertion device is attached and the swing base is in a rising state;

FIG. 10B is a diagram showing the cross section of the washing instrument when the insertion device is attached and the swing base is in a falling state.

DETAILED DESCRIPTION OF THE PREFERRED EMBODIMENT

Hereinafter, embodiments of the present invention will be described in detail with reference to the drawings.

First Embodiment

A washing instrument for an insertion device according to the first embodiment, is described.

Figure 1:
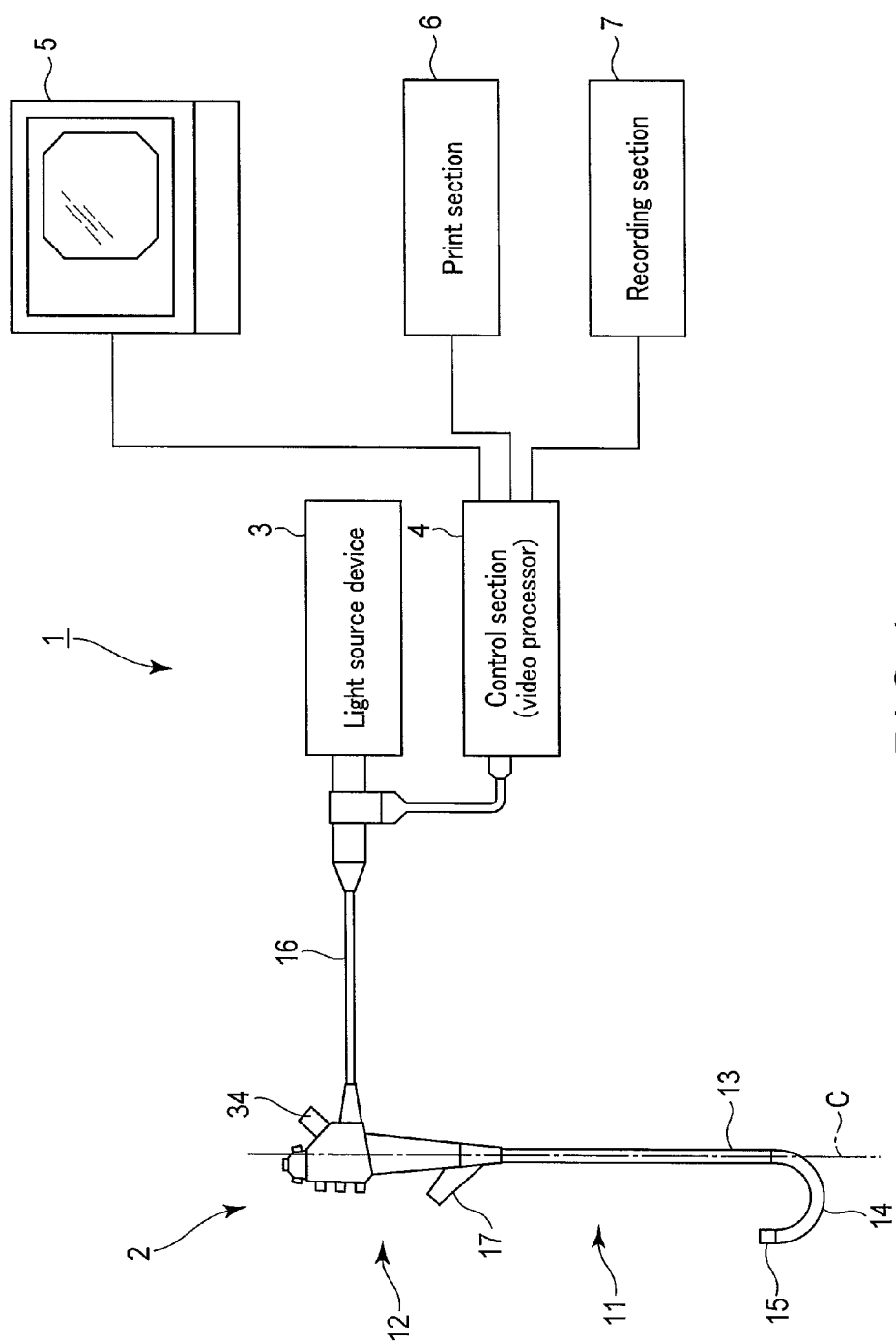
FIG. 1 is a schematic diagram of an insertion system according to a first embodiment of the present invention.
Figure 2A:
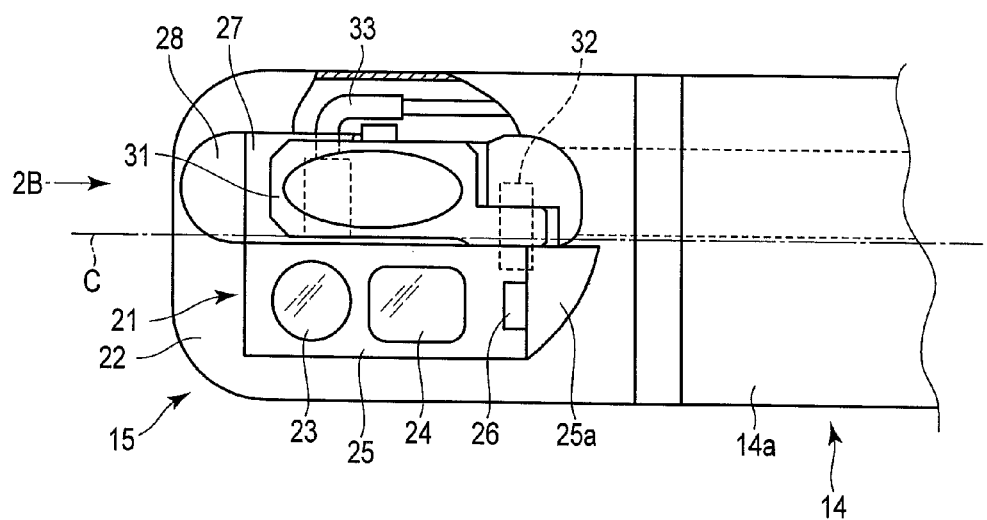
FIG. 2A is a top view of a distal configuration portion in the first embodiment.
Figure 2B:
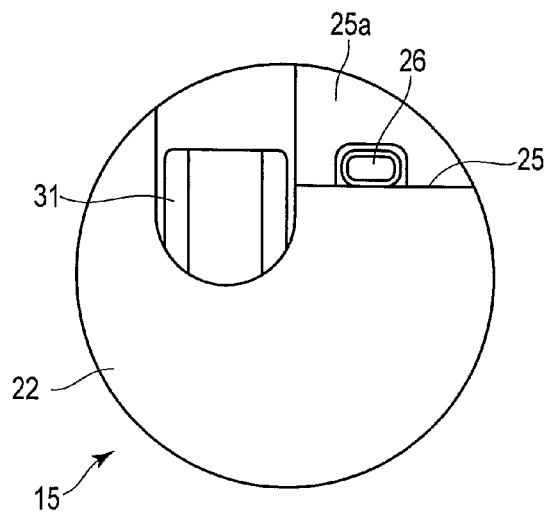
FIG. 2B is a front view of the distal configuration portion seen from an arrow 2B side shown in FIG. 2A.

A distal configuration portion including a treatment instrument swing base (hereinafter referred to as a swing base) provided at the distal end of an insertion portion of an endoscope apparatus is first described as an example of a washing target for the washing instrument according to the present embodiment. FIG. 1 is a diagram showing a system configuration of the endoscope apparatus to be the washing target. FIG. 2A is a top view of the distal configuration portion including the swing base provided at the distal end of the insertion device. FIG. 2B is a diagram showing the external configuration in which the distal configuration portion is seen from the front surface (an arrow 2B: FIG. 2A). FIG. 3 is a diagram showing the configuration of the cross section of the swing base in a falling state in the distal configuration portion shown in FIG. 2A.

As shown in FIG. 1, an endoscope apparatus 1 mainly comprises an insertion device 2 serving as an endoscope body, a light source device 3 which supplies illumination light to the insertion device 2, a control section 4 including a video processor which subjects, to image processing, a video signal obtained by an unshown imaging unit provided at the distal end of the insertion device 2, a display section 5 which displays an obtained a (4b@h observation image and information regarding this image, a print section 6 which prints the image information including the observation image displayed on the display section 5, and a recording section 7 which records the video signal.

Although the medical endoscope apparatus is an example of the insertion device here, the insertion device does not need to be thereto. The insertion device 2 can otherwise be washed by the washing instrument according to the present embodiment as long as the insertion device 2 is an insertion device such as an industrial endoscope or a catheter or an over tube having no illumination optical system and no observation optical system in which an aperture section or a portion to be the washing target is configured to be put in and out from the circumferential surface side.

As shown in FIG. 1, the insertion device 2 mainly comprises an insertion portion 11 and an operating section 12. The insertion portion 11 has a flexible tubular portion 13 which is coupled to the operating section 12 and which has flexibility, a curving portion 14 which is coupled to the distal end of the flexible tubular portion 13, and a distal end constituting section 15 which is internally equipped with a swing base provided at the distal end of the curving portion 14. The operating section 12 is connected to the light source device 3 and the control section 4 by a universal cord 16. A forceps opening 17 to introduce, for example, a forceps into the insertion portion is provided between the proximal end of the insertion portion 11 and the operating section 12.

As shown in FIG. 3, the distal end constituting section 15 which is the distal end of the insertion device is coupled to the curving portion 14 by the fitting of a node ring 14a at the distal end of the curving portion 14 into the distal end constituting section 15. The distal end constituting section 15 has a body portion 21 made of a metal such as SUS, and the circumferential surface of the body portion 21 is covered with a cover portion 22 having electric insulation.

As shown in FIG. 2A and FIG. 2B, a part of an outer peripheral surface of the distal end constituting section 15 is flattened, and the flattened part is divided into two parts in a longitudinal direction so that a flat observation surface 25 is formed on one side, and an aperture section 27 is formed on the other side. In the observation surface 25, there are disposed an illumination window portion 23 to emit illumination light, and an observation window portion 24 in which an unshown image pickup device is disposed. A nozzle portion 26 is provided in the vicinity of this observation surface 25, and spouts out a washing liquid such as physiological saline so that the illumination window portion 23 and the observation window portion 24 are suitably washed. This observation surface 25 is a reference position (reference surface) for a later-described rotation direction regulating portion 42h.

As shown in FIG. 3, the aperture section 27 on the other side opens in the circumferential surface (side circumferential surface) of the distal end constituting section 15. In a receiving chamber (or a swing base receiving chamber) 28 in the aperture section 27, a treatment instrument swing base (hereinafter referred to as the swing base) 31 is swingably disposed. C shown in FIG. 1 and FIG. 3 is a direction in which the insertion portion 11 and the distal end constituting section 15 lie long, and indicates an axial direction.

The swing base 31 is rotatably supported on a raising shaft 32, and is coupled to a raising operation portion 31 provided in the operating section 12 by a pull wire 33. The front side of the swing base 31 which abuts on, for example, a forceps to change the movement direction is a raising surface, and the back side of the swing base 31 is a back surface. The swing base 31 rotates by the operation of the raising operation portion 34 and thus rises or falls. In this way, the swing base 31 and its drive mechanism, are housed in the narrow swing base receiving chamber 28 in this way, it is difficult to remove contamination resulting from bodily fluids and living tissue fragments adhering to, for example, the periphery of the raising shaft 32 and parts such as the back surface of the swing base 31 that is shadowed when seen from the aperture section 27.

Next, a washing instrument 41 according to the first embodiment is described.

FIG. 4 is a diagram showing the external configuration of the washing instrument according to the present embodiment. FIG. 5 is a diagram showing a state where the insertion device is attached to the washing instrument and thus washed. FIG. 6 is a diagram in which the washing instrument without the insertion device attached thereto is seen from the front surface side. FIG. 7A is a diagram in which the washing instrument with the insertion device attached thereto is seen from the front side. FIG. 7B is a diagram showing the cross section of the washing instrument with the insertion device attached thereto. In the washing instrument described below, the side where the distal end constituting section 15 is plugged in is the back side of the washing instrument, and the side on which the distal end of the distal end constituting section 15 abuts is the front side.

As shown in FIG. 6, FIG. 7A, and FIG. 7B, a washing instrument body 42 has inside a circularly cylindrical housing space to attach the distal end constituting section 15. Although the external shape is circularly cylindrical in the present embodiment, the external shape is not limited as long as the inside has a hollow shape that allows the attachment of the distal end constituting section 15, and the external shape may be a rectangular box shape.

The washing instrument 41 has the washing instrument body [housing portion] 42 having a hollow receiving chamber to which the distal end constituting section 15 of the insertion device 2 is attached, an injection tube 43 which is coupled to a first joint portion 42i of the washing instrument body 42, an injection tube 44 which is coupled to a second joint portion 42j, a three-way cock [liquid supply selecting portion] 45 which switches communication directions, a syringe 46 to supply a washing liquid, a T-shaped syringe coupling portion 47 in which a syringe attachment end 47a to attach the syringe 46 to is open, a suction tube 48 which extends from a branched water suction end 47d of the syringe coupling portion 47, and an injection tube 49 which extends to the three-way cock 45 from a liquid supply end 47e.

The first joint portion 42i has a first washing opening 42a which opens to the inner and front side of the washing instrument body 42 and which functions as a nozzle, and a washing liquid or the like is supplied to the first washing opening 42a from the injection tube 43 which serves as a liquid supply path. Similarly, the second joint portion 42j has a second washing opening 42b which opens to the inner and back side of the first washing opening 42a and which functions as a nozzle, and a washing liquid or the like is supplied to the second washing opening 42b from the injection tube 44 which serves as a liquid supply path. At a water suction opening of the suction tube 48, a cylindrical weight 50 which doubles as, for example, a water suction opening is provided to be disposed in the vicinity of the bottom side without floating on the water when the water is supplied.

This weight 50 can be extended without bending partway to ensure the open state of the pipeline if the suction tube 48 which serves as a liquid supply path is soft. If the injection tubes 43 and 44 and the washing instrument body 42 have an attachment/detachment structure, the washing instrument body 42 suited to the type of distal end constituting section 15 can be selectively attached, and the used washing instrument body 42 alone can be disposed of.

As shown in FIG. 6, FIG. 7A, and FIG. 7B, the washing instrument body 42 has a charging hole 42c provided on the back side to plug in the distal end constituting section 15, a rotation direction regulating portion 42h provided in the upper inner surface in the vicinity of the center so that the observation surface 25 of the distal end constituting section 15 faces the rotation direction regulating portion 42h, an axial direction regulating portion 42d provided on the front side on which the distal end constituting section 15 abuts for positioning, and an opening 42f for the washing liquid to come out. The rotation direction regulating portion 42h and the axial direction regulating portion 42d are movement regulating portions.

When the distal end constituting section 15 is inserted into the washing instrument body 42 so that the distal end of the distal end constituting section 15 abuts on a positioning wall 42g of the axial direction regulating portion 42d, positioning is also achieved in the rotation direction regulating portion 42h, and both the rotation direction and the axial direction of the distal end constituting section 15 are positioned accordingly. Further, the swing base 31 is raised by the operation of the raising operation portion 34 into abutment, with an upper inner surface 42k of the washing instrument body 42 so that the positioning state will be maintained.

The first washing opening 42a and the second washing opening 42b of the washing instrument body 42 are described.

The first washing opening 42a has a central axis d1 (which is the same as the central axis of the first joint portion 42i) provided to be offset to the outer circumferential side relative to a central axis d in the diametrical direction of the washing instrument body 42 in a flow path which is straight in a parallel direction. If a washing liquid 63a which is a washing liquid [fluid for washing] is spouted out in the direction of this central axis d1, the washing liquid 63a flows to detour from the distal side of the swing base 31 to the back side thereof to achieve washing, and discharges adherent matter from the opening 42f together with a used washing liquid 63, as shown in FIG. 7A and FIG. 7B.

The second washing opening 42b is provided so that a central axis d2 (which is the same as the central axis of the second joint portion 42i) is inclined in a direction aslant to the outer circumferential side relative to the central axis d in the diametrical direction of the washing instrument body 42, as shown in FIG. 7A and FIG. 7B. The flow path of the second joint portion 42j is bent partway toward a place to gull out the pull wire 33. A washing liquid 63b spouts out from the second washing opening 42b to the pull wire 33 and its periphery and washes the same, and discharges adherent matter from the opening 42f together with the used washing liquid 63.

Both the injection tubes 43 and 44 are coupled to the respective liquid supply openings of the three-way cock 45. The washing liquid is supplied to a water suction opening of the three-way cock 45 via the syringe coupling portion 47 and the suction tube 48. The three-way cock 45 spouts out the washing liquid from one of the injection tubes 43 and 44, that is, one of the first washing opening 42a and the second washing opening 42b by switching.

The syringe coupling portion 47 is T-shaped to branch into three directions, and functions as a pump when check valves 47b and 47c are provided in two openings and the syringe 46 is coupled to the other opening. As shown in FIG. 4, the syringe 46 is attached to the syringe attachment end 47a. If a plunger 46a of the syringe 46 is pulled out, the internal pressure of the syringe 46 becomes a negative pressure, and the washing liquid 63 flows in. If the plunger 46a is pushed in, the internal pressure of the syringe 46 becomes a positive pressure, and the washing liquid 63 flows out.

The check valves 47b and 47c may have a known structure such as a structure having a valve which blocks a hole made in a partition plate by urging force and which opens and closes in response to the pressure resulting from a fluid. The syringe coupling portion 47 has the check valve 47c provided in the liquid supply end 47e so that the check valve 47c becomes open if the valve rotates outward at the positive internal pressure and so that the check valve 47c is sucked by the partition plate and becomes closed at the negative pressure. The check valve 47b is also provided in the liquid supply end 47e, and the check valve 47b becomes open if the valve rotates inward at the negative internal pressure and, whereas the check valve 47b is pressed to the partition plate and becomes closed at the positive pressure.

Next, washing of the distal end constituting section 15 of the insertion device 2 using the washing instrument 41 according to the present embodiment is described. FIG. 5 shows a state where the distal end constituting section 15 of the insertion device 2 is attached to the washing instrument 41 shown in FIG. 4.

The distal end constituting section 15 is attached to the washing instrument body 42 of the washing instrument 41 by positioning as described above, and the distal end constituting section 15 is placed in a drain tray 61. It is assumed that the washing liquid 63 is put in the drain tray 61 in advance and the washing instrument body 42 is sunk in the water to prevent the washing liquid from scattering around the drain tray 61 when the washing liquid is swiftly discharged from the opening 42f. A tray cover to prevent scattering may be additionally prepared attachably to the upper part of the tray.

The suction hole 50 of the suction tube 48 is then disposed to be sunk in a water suction tray 62 which is filled with the washing liquid 63. In addition, the three-way cock 45 is switched to set whether to spout out the washing liquid from the first washing opening 42a or the second washing opening 42b. While any one of the washing openings may be selected, the washing liquid can flow by any distribution depending on the adjustment of the three-way cock 45: about 30% at the first washing opening 42a, and about 70% at the second washing opening 42b.

The plunger 46a of the syringe 46 is then repetitively pushed and pulled, and the washing liquid 63 in the water suction tray 62 is drawn into and fills the syringe coupling portion 47. Further, the washing liquid 63 is supplied to the selected washing openings 42a and 42b from the injection tube 49 via the three-way cock 45 by the push-in of the plunger 46a, and the washing liquid 63 spouted out from these washing openings directly collides with the inside of the swing base receiving chamber 28 including the swing base 31, and then achieves washing. The used washing liquid is sequentially discharged to the drain tray 61 from the swing base receiving chamber 28 through the opening 42f together with adherent matter.

In the present embodiment (including the second to fourth embodiments described below), the washing instrument body 42 and the drain tray 61 are preferably made of a transparent material. When the transparent material is used, the degree of decontamination can be easily checked from the outside. Although the washing instrument body 42 has the openings formed at both the front and back ends, the distal end constituting section 15 of an insertion device such as an endoscope may be configured to have not only the opening 42f at the distal end but also a large clearance (see FIG. 7B) between the distal end constituting section 15 and the washing instrument body 42 so that the used washing liquid and contamination may easily flow out. Liquid supply means such as a liquid supply pump may be used instead of the syringe which supplies the washing liquid.

According to the washing instrument 41 in the present embodiment described above, the swing base is fixed in a drawn-up state at the time of attachment to the washing instrument body, and the washing liquid spouted out from the washing openings therefore flows to detour to the back side of the swing base, thereby achieving efficient washing. Because washing is performed alternatively from two places, the water flows out so that the two water flows do not interfere with the washing. Moreover, if the washing instrument body 42 is formed into a hollow shape in accordance with the type of distal end constituting section 15 to be the washing target, it is possible to wash an existing insertion device 2 having any shape. The washing liquid can be independently or simultaneously and continuously spouted out to multiple washing target places to achieve washing by one positioning at the time of attachment, and the volume of the liquid supply can also be independently adjusted. Therefore, the washing instrument according to the present embodiment can obtain high washing performance for an insertion device having a complicated structure without the addition of any special equipment on the insertion device side, and provide sanitariness and high convenience. The washing liquid may spout out from two places in different spouting directions, in the same direction, or in parallel directions.

Second Embodiment

Figure 8:
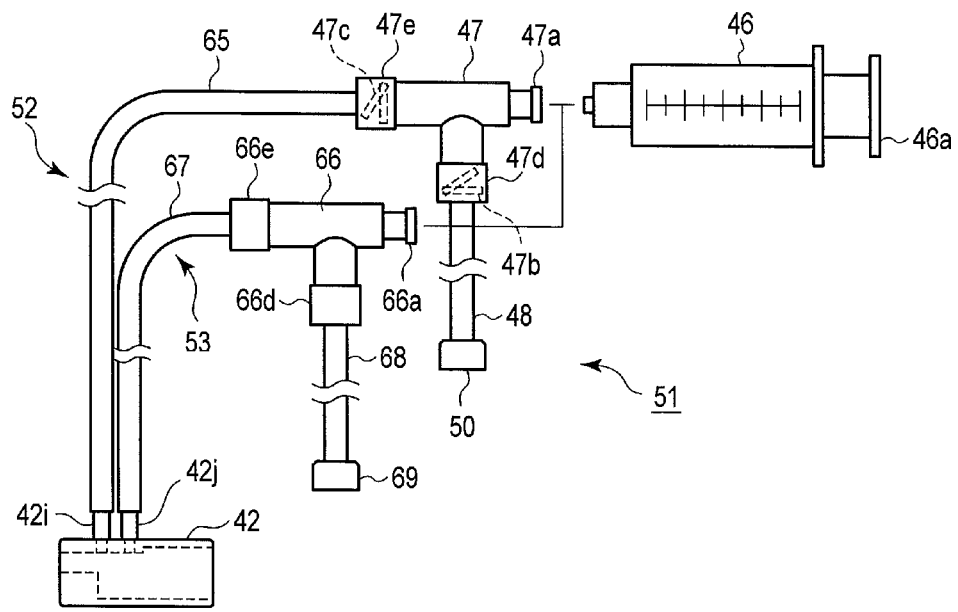
FIG. 8 is a diagram showing the external configuration of a washing instrument for the insertion device according to a second embodiment.

FIG. 8 is a diagram showing the external configuration of a washing instrument for the insertion device according to the second embodiment. In the configuration according to the present embodiment, an independent liquid supply path is formed for each of the first and second washing openings 42a and 42b without the use of the three-way cock 45. In the following explanation, components equivalent to those in the first embodiment described above have the same reference marks and are not described in detail.

A washing instrument 51 according to the present embodiment has a first liquid supply path 52 to supply the washing liquid to the first washing opening 42a, and a second liquid supply path 53 to supply the washing liquid to the second washing opening 42b. The first liquid supply path 52 is directly coupled to the first joint portion 42i of the washing instrument body 42 from the liquid supply end 74e of the syringe coupling portion 47 via an injection tube 65, and communicates with the first washing opening 42a. The second liquid supply path 53 is directly coupled to the second joint portion 42j of the washing instrument body 42 from a liquid supply end 66e of a syringe coupling portion 66 via an injection tube 67, and communicates with the second washing opening 42b. A water suction end 66d of the syringe coupling portion 66 is provided with an injection tube 68, and a weight 69 is attached to the distal end of this tube. Here, the syringe coupling portion 66 has an equivalent configuration having the syringe coupling portion 47 and check valve described above, and functions as a pump when the syringe 46 is connected to the syringe coupling portion 66.

FIG. 8 shows an example in which one syringe 46 is coupled to one of the two syringe coupling portions 47 and 66 to supply the washing liquid 63. In this case, the syringe 46 needs to be replaced by an operator when the washing openings for the washing liquid 63 are changed. In contrast, it is only necessary to alternatively push and pull the plunger 46a by attaching the syringe 46 to each of the syringe coupling portions 47 and 66.

If there are two operators, it is possible to alternatively or simultaneously supply a large volume of washing liquid by pushing and pulling the plungers 46a of two syringes 46.

As described above, it is possible to obtain a washing instrument similar to that according to the first embodiment described above by constructing a liquid supply path in each of the washing openings 42a and 42b without the use of the three-way cock 45. Therefore, the present embodiment enables functional advantages equivalent to those according to the first embodiment described above to be obtained. Moreover, because it is not necessary to switch the liquid supply paths, washing can be achieved with a large volume of alternatively or simultaneously supplied washing liquid when two operators are in charge of washing work.

Third Embodiment

Figure 9:
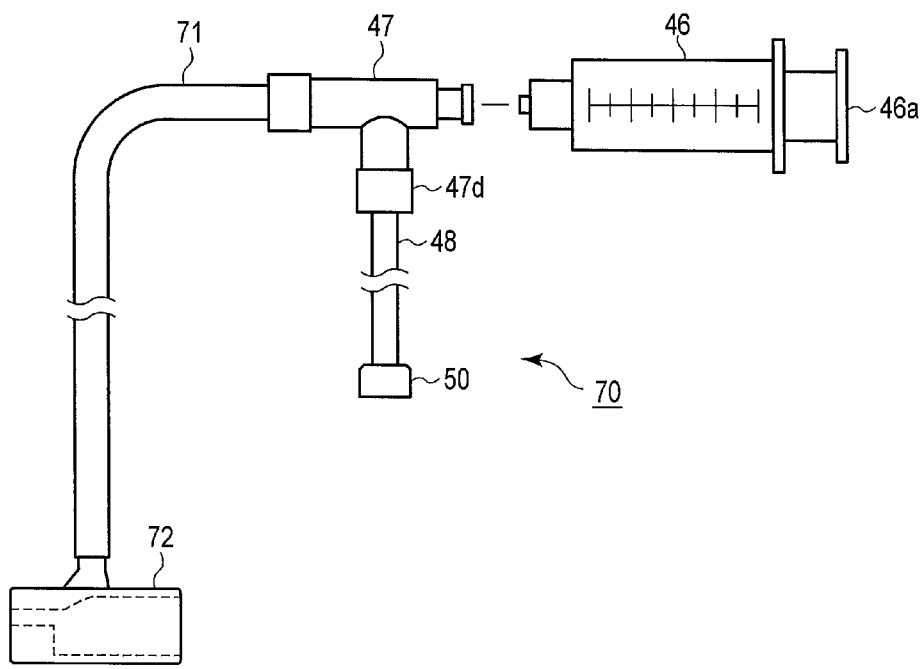
FIG. 9 is a diagram showing the external configuration of a washing instrument for the insertion device according to a third embodiment.

FIG. 9 is a diagram showing the external configuration of a washing instrument for the insertion device according to the third embodiment. FIG. 10A is a diagram showing the cross section of the washing instrument when the insertion device is attached and the swing base is in a rising state. FIG. 10B is a diagram showing the cross section of the washing instrument when the insertion device is attached and the swing base is in a falling state. In the following explanation, components equivalent to those in the first embodiment described above have the same reference marks and are not described in detail.

A washing instrument 70 according to the present embodiment has a washing instrument body 42 to which the distal end constituting section 15 is attached, an injection tube 71 which is coupled to a joint portion of the washing instrument body 42, the syringe coupling portion 47 which is coupled to the inject ion tube 71, the suction tube 48 which extends from the branched water suction end 47d of the syringe coupling portion 47, the cylindrical weight 50 which prevents floating and which doubles as a water suction opening of the suction tube 48, and the syringe 46 to supply a washing liquid.

The washing instrument body 72 is described with reference to FIG. 10A and FIG. 10B.

The washing instrument body 72 according to the present embodiment is configured so that one flow path 72g through which the washing liquid 63 supplied from one supply opening flows is divided into two parallel flow paths 72i and 72j inside the washing instrument body 72, and the washing liquid 63 is supplied to each of first and second washing openings 72a and 72b.

The washing instrument body 72 has a charging hole 72c provided on the back side to plug in the distal end constituting section 15, a rotation direction regulating portion (not shown, see the mark 42e in FIG. 7A) provided in the upper inner surface to face the observation surface 25 of the distal end constituting section 15 described above, an axial direction regulating portion 72d provided on the front side on which the distal end constituting section 15 abuts for positioning, and an opening 72f for the washing liquid 63 to escape.

As shown in FIG. 10A, when the distal end constituting section 15 is inserted into the washing instrument body 72 so that the distal end of the distal end constituting section 15 abuts on a positioning wall 72e of the axial direction regulating portion 72d, positioning is also achieved in the rotation direction regulating portion 42h, and the rotation direction in the axial direction of the distal end constituting section 15 is also positioned accordingly.

The flow paths 72g, 72i, and 72i and the first and second washing openings 72a and 72b of the washing instrument body 72 are described. The flow path 72g in the joint portion to which the injection tube 71 is coupled is divided into the two flow paths 72i and 72j, and the quid supply direction (a central axis direction: a vertical direction in FIG. 7A) of the washing liquid 63 is bent to the distal side in the branched part. The first and second washing openings 72a and 72b are disposed so that the washing liquid 63 is spouted out to the aperture section 27 of the distal end constituting section 15 parallel at different positions inside the swing base receiving chamber 28 at the same angle obliquely from the back. In the present embodiment, the first washing opening 72a is disposed at a position to face the distal end of the fallen swing base 31, and the second washing opening 72b is disposed at a position to face the distal end of the risen swing base 31.

Owing to this arrangement, in the distal end constituting section 15 attached to the washing instrument body 42, as shown in FIG. 10A, the distal end of the swing base 31 comes close to the second washing opening 72b and becomes a lid at the position where the swing base 31 maximally rises by the operation of the operation portion, which makes it difficult for the washing liquid 63 to flow. Thus, the washing liquid 63a which accounts for most of the washing liquid 63 is spouted out from the first washing opening 72a, flows to detour to the back side from the distal side of the swing base 31, so that the back side of the swing base 31 and the bottom part of the swing base receiving chamber 28 are washed.

In contrast, as shown in FIG. 10B, the distal end of the swing base 31 comes close to the first washing opening 72a and becomes a lid at the position where the swing base 31 maximally falls by the operation of the operation portion, which makes it difficult for the washing liquid 63 to flow. Thus, the washing liquid 63b which accounts for most of the washing liquid 63 is spouted out from the second washing opening 72b, flows in the raising surface from the distal side of the swing base 31, and directly collides with the periphery of the raising shaft 32 of the swing base 31 and the periphery of the coupling portion of the pull wire 33, so that washing is achieved.

In the present embodiment as well as in the embodiments described above, the plunger 46a of the syringe 46 is repetitively pushed and pulled, and the washing liquid 63 in the unshown water suction tray (the water suction tray 62 shown in FIG. 5) is drawn into and fills the syringe coupling portion 47. Further, the washing liquid 63 is supplied to the washing instrument body 42 from the injection tube 71, divided into two parts as described above, spouted out so that the proportion of water volume is higher in the washing opening to which the distal end of the swing base 31 is not close, and the inside of the swing base receiving chamber 28 including the swing base is washed. The used washing liquid is discharged to the unshown drain tray (the drain tray 61 shown in FIG. 5) from the swing base receiving chamber 28 through the opening 72f together with adherent matter.

As described above, in the present embodiment, the state where each of the first and second washing openings 72a and 72b are blocked is varied by the adjustment of the angle (rising angle) at which the swing base 31 is drawn up, and the ratio between the supply volume of the washing liquid 63a used for washing and the supply volume of the washing liquid 63b can be adjusted.

Thus, for example, the back side of the swing base 31, the periphery of the raising shaft 32 of the swing base 31, and the periphery of the coupling portion of the pull wire 33 can be selectively and strongly washed. In the present embodiment, one injection tube 71 is used, and no three-way cock is used, so that the configuration is simple, cost can be low owing to a small number of components, and the management is easy. Moreover, functional advantages equivalent to those according to the first embodiment described above can be obtained.

Fourth Embodiment

Figure 11:
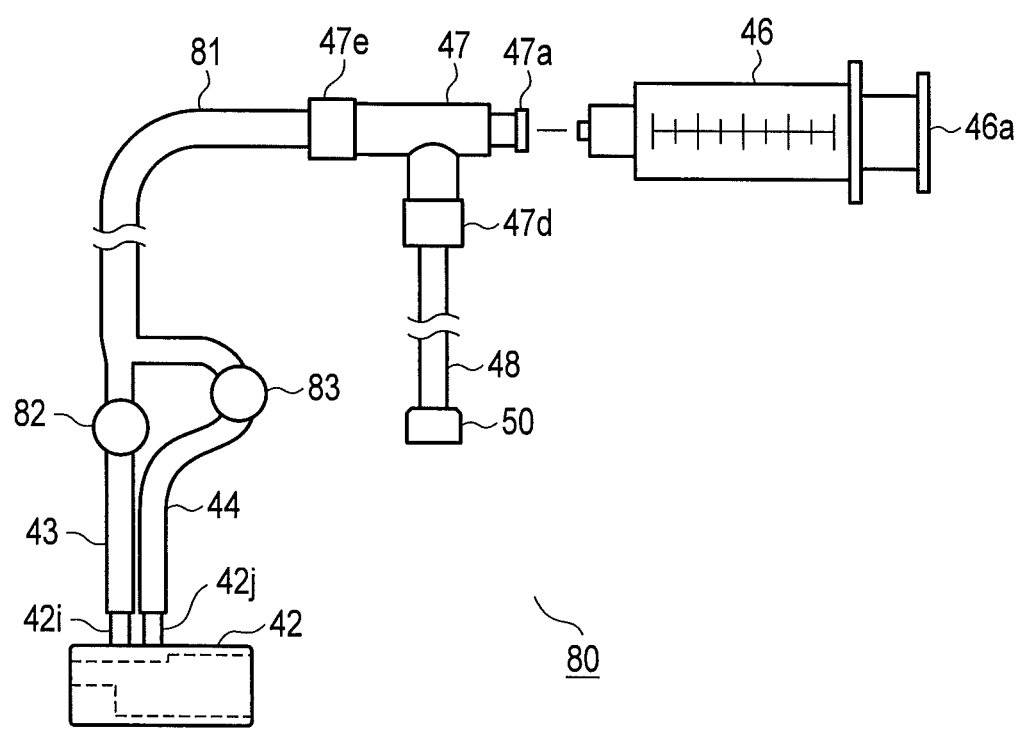
FIG. 11 is a diagram showing the external configuration of a washing instrument for the insertion device according to a fourth embodiment.

FIG. 11 is a diagram showing the external configuration of a washing instrument for the insertion device according to the fourth embodiment. In the configuration according to the present embodiment, two clamp members 82 and 83 are provided to switch the liquid supply to each of the washing openings 42a and 42b without the use of the three-way cock 45. In the following explanation, components equivalent to those in the first embodiment described above have the same reference marks and are not described in detail.

A washing instrument 80 according to the present embodiment has the washing instrument body 42 to which the distal end constituting section 15 is attached, the injection tube 43 which is coupled to the first joint portion 42i of the washing instrument body 42, the first clamp member 82 which is coupled to the injection tube 43, the injection tube 44 which is coupled to the second joint portion 42j, the second clamp member 83 which is coupled to the injection tube 44, the syringe 46 to supply the washing liquid 63, the T-shaped syringe coupling portion 47 in which the syringe attachment end 47a to attach the syringe 46 to is open, an injection tube 81 having a two-way branch coupled to the two clamp members 82 and 83 from the liquid supply end 47e, and the suction tube 48 which extends from the branched water suction end 47d of the syringe coupling portion 47.

The washing instrument 80 can selectively supply liquid to desired one or both of the first and second washing openings 42a and 42b (see FIG. 7A) by using the first clamp member 82 and the second clamp member 83 to pierce or block each liquid supply path. If the first clamp member 82 and the second clamp member 83 are configured to be able to lock partway between full closure and full opening, the ratio of the volumes of supplied liquids flowing through the respective liquid supply paths can also be adjusted. Moreover, functional advantages equivalent to those according to the first embodiment described above can be obtained in the present embodiment as well.

The present invention provides a sanitary and highly convenient washing instrument for an insertion device which enables high washing performance to be obtained even for an insertion device having a complicated structure without the addition of any special equipment on the insertion device side.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A washing instrument for an insertion device comprising:
    a housing portion including a receiving chamber in which the distal end portion of the insertion device provided with an aperture section in a distal-side circumferential surface thereof is attached to the inside;
    a liquid supply path which allows a fluid for washing to flow to the housing portion from the outside;
    a first washing opening which spouts out the fluid from the liquid supply path to the receiving chamber in a first direction that intersects with the axial direction of the distal end portion of the insertion device attached to the housing portion;
    a second washing opening which spouts out the fluid from the liquid supply path to the receiving chamber in a second direction that intersects with the axial direction of the distal end portion of the insertion device attached to the housing portion; and
    a movement regulating portion which is provided in the housing portion, abuts on the distal end portion of the housed insertion device, is opposed to the aperture section, and positions the distal end portion of the insertion device so that the fluid spouted out from the first washing opening and the fluid spouted out from the second washing opening directly collide with different positions inside the aperture sections.

2. The washing instrument for the insertion device according to claim 1, wherein liquid supply path includes a liquid supply selecting portion which selectively supplies the fluid to the first washing opening or the second washing opening.

3. The washing instrument for the insertion device according to claim 2,
    wherein the liquid supply selecting portion adjusts the distribution of the volume of the fluid to be supplied to the first washing opening and the volume of the fluid to be supplied to the second washing opening.

4. The washing instrument for the insertion device according to claim 1,
    wherein the second washing opening spouts out the fluid from the liquid supply path toward the receiving chamber in the second direction different from the first direction.

5. The washing instrument for the insertion device according to claim 1,
    wherein the housing portion has a cylindrical hollow housing chamber to attach the distal end portion of the insertion device to the inside thereof.

6. The washing instrument for the insertion device according to claim 1,
    wherein the aperture section includes therein a swing base which abuts on a treatment instrument extending to the outside and changes the movement direction of the treatment instrument by being connected to a pull wire and rotated to rise or fall with respect to an axis by an operation of the pull wire, and
    the movement regulating portion positions the distal end portion of the insertion device so that the fluid spouted out from the first washing opening or the second washing opening directly collides with at least the swing base in the aperture section as a washing target.

7. The washing instrument for the insertion device according to claim 6,
    wherein the distal end of the swing base abuts on the inner circumferential surface of the receiving chamber so that the swing base is maintained at a position between a position where the swing base maximally falls and a position where the swing base maximally rises in the aperture section in a rotation direction in which the swing base rotates when the distal end portion is positioned, and
    the first washing opening or the second washing opening is configured so that when the swing base is positioned, the first washing opening supplies the fluid to a side closer to the distal end of the insertion device than the swing base and the second washing opening supplies the fluid to a side closer to the proximal end of the insertion device than the swing base, respectively.

8. The washing instrument for the insertion device according to claim 5, further comprising a swing base angle regulating portion which positions the swing base so that the swing base is maintained at a position between a position where the swing base maximally falls and a position where the swing base maximally rises in a rotation direction in which the swing base rotates when the swing base is positioned in the receiving chamber, wherein the first washing opening supplies the fluid more to the distal side of the insertion device than to the swing base when the distal end of the swing base comes close to and blocks the second washing opening, and the second washing opening supplies the fluid more to the proximal side of the insertion device than to the swing base when the distal end of the swing base comes close to and blocks the first washing opening.

9. The washing instrument for the insertion device according to claim 6, wherein when the distal end portion is positioned in the receiving chamber, the first washing opening is disposed at a position to face the distal end of the fallen swing base, and the second washing opening is disposed at a position to face the distal end of the risen swing base, when the distal end portion is positioned in a state where the swing base has risen in the aperture section, the first washing opening spouts out the fluid toward the back side of the risen swing base, and when the distal end portion is positioned in a state where the swing base has fallen in the aperture section, the second washing opening spouts out the fluid toward a raising shaft which supports the swing base.

10. The washing instrument for the insertion device according to claim 1, wherein the movement regulating portion includes:

an axial direction regulating portion which is provided in the housing portion, abuts on the distal end portion of the housed insertion device, and positions the insertion device; and a rotation direction regulating portion which is provided in the housing portion, and is opposed to the aperture section of the housed insertion device to regulate a rotation direction of the insertion device.

* * * * *